United States Patent [19]

Steinetz, Jr.

[11] 4,062,964

[45] Dec. 13, 1977

[54] ANTIFERTILITY-COMBINATIONS

[75] Inventor: Bernard George Steinetz, Jr., Franklin Lakes, N.J.

[73] Assignee: Ciba-Geigy Corporation, Ardsley, N.Y.

[21] Appl. No.: 729,571

[22] Filed: Oct. 4, 1976

Related U.S. Application Data

[63] Continuation-in-part of Ser. No. 637,333, Dec. 3, 1975, abandoned.

[51] Int. Cl.$^2$ ............... A61K 31/445; A61K 31/215; A61K 31/19
[52] U.S. Cl. ................... 424/267; 424/275; 424/285; 424/305; 424/317
[58] Field of Search ............ 424/267, 268, 305, 317, 424/285, 275

[56] References Cited

U.S. PATENT DOCUMENTS

| 3,814,809 | 6/1974 | Gordon et al. | 424/305 |
| 3,836,659 | 9/1974 | Steinetz | 424/268 |
| 3,899,587 | 8/1975 | Pharriss | 424/305 |

*Primary Examiner*—Sam Rosen
*Attorney, Agent, or Firm*—Theodore O. Groeger

[57] ABSTRACT

Sub-abortifacient doses of $\alpha$-(4-aminophenyl)-$\alpha$-lower alkylglutarimides and natural prostaglandins or corresponding 9-oxa or 9-thiaprostaglandins, when given in combination to impregnated female mammals in the early period of gestation, or after a missed menses, terminate pregnancy effectively and without undue side effects.

9 Claims, No Drawings

ANTIFERTILITY-COMBINATIONS

CROSS-REFERENCE TO RELATED APPLICATION

This is a continuation-in-part of application Ser. No. 637,333, filed Dec. 3, 1975 (now abandoned).

BACKGROUND OF THE INVENTION

The shortcomings of the "pill" and the various intrauterine devices have lent impetus to the continuing search for safe, simple and effective means of contraception. Medicinal induction of very early abortion or resorption of embryos offers a practical way of dealing with unwanted pregnancies, because an interceptive drug would only require use after a missed menses. Early work on the prostaglandins suggested that this type of compounds might serve as a practical early abortifacient. Subsequent studies revealed their side effects, which are severe enough to make it unlikely that these drugs could be used in the home on a prescription basis. Furthermore, the mechanism of action of natural prostaglandins, or 9-oxa- or-thiaprostaglandins, appears to differ between various animal species, including rodents and subhuman primates, as compared with human beings. In the former, they may disrupt the function of the corpus luteum, while in the latter their action appears to be mainly oxytocic.

Another type of drug, aminoglutethimide, has aroused interest because it blocks the conversion of cholesterol to pregnenolone in the steroid pathway. It inhibits progesterone secretion in pregnant and non-pregnant animals and human beings and can be used, according to U.S. Pat. No. 3,836,659, for reducing the number of fetuses in pregnant females. Unfortunately, $\alpha$-(4-aminophenyl)-$\alpha$-lower alkylglutarimides have a low potency and short duration of action for inducing abortion in rats. They must be given in high doses, which cause marked side effects, i.e. their originally discovered anticonvulsant effects, including central nervous system depression.

Surprisingly it was found that the natural prostaglandins and analogs thereof, e.g. those disclosed in U.S. Pat. Nos. 3,657,328, 3,678,092 or J. Pharm. Sci. 61, 1861 (1972), as well as 9-oxa- and 9-thiaprostaglandins, e.g. those disclosed in U.S. Pat. Nos. 3,883,659 and 3,970,670, despite the extremely short duration of action of the natural products, and in doses which individually did not interfere with pregnancy, synergistically enhance the interceptive action of said glutarimides, also given in doses markedly below those taught in U.S. Pat. No. 3,836,659, resulting in the resorption of all or most fetuses.

SUMMARY OF THE INVENTION

The present invention concerns and has for its object the provision of a new pharmaceutical composition comprising:

a. a pharmacologically ineffective amount of an $\alpha$-(4-aminophenyl)-$\alpha$-lower alkylglutarimide, or its lower alkanoyl derivative corresponding to Formula I

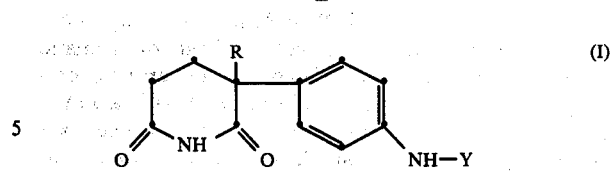

wherein R is lower alkyl and Y is hydrogen or lower alkanoyl, or a therapeutically acceptable acid addition salt thereof;

b. a pharmacologically ineffective amount of a natural prostaglandin, or analogs thereof corresponding to Formula II

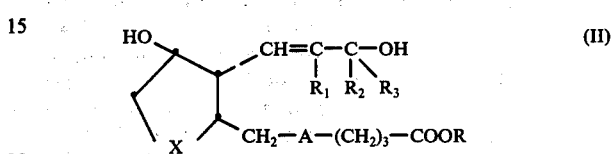

wherein A is methylene, ethylene or ethenylene, X is carbonyl, hydroxymethylene, oxa, thia, sulfinyl or sulfonyl, each of $R_1$ and $R_2$ is hydrogen or lower alkyl, each of R and $R_3$ are an aliphatic, cycloaliphatic, cycloaliphatic-aliphatic or araliphatic radical, or R is hydrogen or one base-equivalent, such as an alkali metal, one equivalent of an alkaline earth metal, ammonium, mono-, di or tri-lower alkyl-, or mono-, di or trihydroxyalkylammonium; whereby both of said amounts together are so selected to cause interception in mammals and c. a pharmaceutical excipient; as well as a new method of terminating pregnancy in mammals by administering to a mated or impregnated female mammal enterally or parenterally a single or multiple dose of said composition.

DESCRIPTION OF THE PREFERRED EMBODIMENTS

The active ingredients I of the compositions claimed herein are either the racemates disclosed in U.S. Pat. No. 2,848,455 or preferably the dextrorotatory antipodes thereof, disclosed in U.S. Pat. No. 3,944,671.

Especially useful for said purpose is the compound of Formula I, wherein R is ethyl and Y is hydrogen, i.e. aminoglutethimide=AG (Elipten ®), or advantageously the dextrorotatory antipode, or said acid addition salts thereof.

In the active ingredients II an aliphatic radical R or $R_3$ represents preferably lower alkyl, as is the case with $R_1$ and $R_2$, e.g. methyl, ethyl, n- or i-propyl, -butyl, -pentyl, -hexyl or -heptyl; lower alkenyl, e.g. allyl or methallyl; or lower alkynyl, e.g. ethynyl or propargyl. The term "lower" referred to above and hereinafter in connection with organic radicals or compounds respectively, defines such with up to 7, preferably up to 4, carbon atoms. $R_3$ also represents higher alkyl, especially such with 8 to 12 carbon atoms, such as n- or i-octyl, -nonyl, -decyl, -undecyl or -dodecyl.

Said cycloaliphatic or cycloaliphatic-aliphatic radicals R and $R_3$ are preferably 3 to 7 ring-membered cycloalkyl, cycloalkenyl or (cycloalkyl or cycloalkenyl)-lower alkyl groups, e.g. cyclopropyl, cyclobutyl, cyclopentyl or cyclohexyl; cyclopent-1-enyl or cyclohex-1 or 3-enyl; cyclopropylmethyl, cyclobutylmethyl, 1- or 2-cyclopentylethyl; cyclopent-3-enylmethyl or cyclohex-1-enylmethyl.

Said araliphatic radicals R or $R_3$ are preferably isocyclic, or heterocyclic, monocyclic radicals of aromatic character substituting one of said aliphatic groups, preferably a lower alkyl group, either directly or via a linking oxygen or sulfur atom, such as (phenyl, phenoxy, furyl or thienyl)-lower alkyl, unsubstituted or substituted in the aromatic ring, preferably the phenyl ring, by one or more than one, especially one or two, of the same or different substituents, such as lower alkyl, e.g. methyl, ethyl, n- or i-propyl or -butyl; lower alkoxy, e.g. methoxy, ethoxy, n- or i-propoxy or butoxy; lower alkylenedioxy, e.g. methylenedioxy, 1,1- or 1,2-ethylenedioxy; halogeno, e.g. fluro, chloro, bromo or iodo; trifluoromethyl; nitro or amino, such as di-lower alkylamino, e.g. dimethylamino or diethylamino. Said aliphatic radicals, especially lower alkyl groups $R_3$, can also be substituted by one of said lower alkoxy groups or one, or up to the maximum number of halogen atoms, as is the case in trifluoromethyl, 2-(methoxy, ethoxy, chloro, bromo or iodo)-ethyl, -propyl or -butyl, 2,2-dichloroethyl, -propyl or -butyl, 2,2,2-trichloroethyl, 3-(methoxy, ethoxy, chloro or bromo)-propyl or -butyl, 4-(methoxy or chloro)-butyl.

Preferred are compounds of Formula II, in which each of R and $R_3$ is lower alkyl, lower alkenyl, lower alkynyl, (3 to 7 ring-membered cycloalkyl or cycloalkenyl)-$C_mH_{2m}$ wherein $m$ is an integer from 0 to 4, (Ph, PhO or Hc)-$C_nH_{2n}$, wherein Ph is phenyl, (lower alkyl)-phenyl, (lower alkoxy)-phenyl, (lower alkylenedioxy)-phenyl, (halogeno)-phenyl, (trifluoromethyl)-phenyl, (nitro)-phenyl or (di-lower alkylamino)-phenyl, Hc is furyl or thienyl and $n$ is an integer from 1 to 4, R is also hydrogen, an alkali metal or one equivalent of an alkaline earth metal and $R_3$ is also (lower alkoxy or halo)-lower alkyl, A is ethylene or ethenylene, $R_1$ and $R_2$ are hydrogen or lower alkyl, and X is carbonyl, hydroxymethylene, oxa, thia, sulfinyl or sulfonyl.

Especially useful for said purpose are compounds of Formula II, wherein R is hydrogen, sodium, potassium or alkyl with up to 4 carbon atoms, each of $R_1$ and $R_2$ is hydrogen, A is ethylene of cis-ethenylene, X is carbonyl, β-hydroxymethylene (i.e. cis vs. the acidic chain), oxa, thia, sulfinyl or sulfonyl, and $R_3$ is n-(pentyl, pent-2-enyl, hexyl or heptyl), (cyclopropyl, cyclopentyl, cyclohexyl, Ph', Ph'O or 2-furyl)-methyl or -ethyl, wherein Ph' is phenyl, tolyl, anisyl, fluorophenyl, chlorophenyl or trifluoromethylphenyl, advantageously prostaglandin $F_{2\alpha}$ i.e. $PGF_{2\alpha}$.

The efficacy of the compositions according to the invention is demonstrable in animal tests, using advantageously mammals, such as rats, hamsters or baboons, as test objects. Thus, for example, adult female rats weighing 190–250 grams are housed in a "reverse room" as described in Contraception 3, 347 (1971), with the exception that the animals have 14 hours of light between 5 P.M. and 7 A.M., and 10 hours of darkness from 7 A.M. to 5 P.M. They are placed with adult male rats from 10 A.M. to 2 P.M. (i.e. "their midnight" ± 2 hours) following which vaginal smears are obtained. Females exhibiting spermatozoa in their smears are assumed to be pregnant (day "0") and isolated for use in the experiments to be described.

Said antifertility compounds may be administered orally, e.g. in suspension with the excipient compraising 3% (by weight) of carboxymethylcellulose, 1.05% methylcellulose, 0.8% sodium chloride, 0.1% polysorbate 80 and 0.002% thimerosal in water, as a single dose on day 5 of pregnancy (i.e. the day after implantation unless otherwise specified). Prostaglandins may be injected subcutaneously twice (9 A.M. and 3 P.M.) on days 4–7 in a conventional 0.1M phosphate buffer at pH = 7.45. Aminoglutethimide phosphate can also be administered in aqueous solution orally, subcutaneously, intraperitoneally or intravenously. The rats are sacrificed on day 10 or 11 of pregnancy and the uterus is examined for living and dead fetuses and implantation sites. The terms "abortion" and "resorption" are used interchangeably because by day 10 or 11 the uterine scars resulting from either event are indistinguishable by gross inspection.

The new method for terminating pregnancy in mammals consists in administering to them enterally or parenterally an interceptive amount of said new compositions, preferably at a dosage level of about 0.1 to 50 mg/kg/day, especially 0.1 to 10 mg/kg/day of compounds I; and about 0.001 to 1 mg/kg/day, especially 0.001 to 0.1 mg/kg/day of compounds II, either in a single (preferred) or multiple, e.g. oral or intramuscular, administration. Said lower dosage levels, e.g. between about 0.1 and 1 mg/kg/day of compounds I and between about 0.001 and 0.01 mg/kg/day of compounds II are chosen for parenteral, e.g. intravenous or intrauterine, administration in the early periods of pregnancy, e.g. days 1 to 30 after mating and/or after a missed menses. A multiple administration is rarely necessary and may not exceed 3 consecutive days.

The pharmaceutical excipient, mentioned under item (c) is preferably such for enteral administration, e.g. for tablets, capsules or suppositories, comprising the active ingredients of Formulae I and II, together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) adsorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. Said pharmaceutical compositions may also contain other therapeutically valuable substances. They are prepared according to conventional mixing, granulating or coating methods respectively, and contain about 1 to 90%, preferably about 2 to 50% of the active ingredient by weight.

The following examples are intended to illustrate the invention and are not to be construed as being limitations thereon.

EXAMPLE 1

Preliminary experiments using large single or daily oral doses of aminoglutethimide phosphate≡AGP revealed that rats were very resistant to the abortifacient activity of this compound, although progesterone levels were decreased more than 70%. But the compound was abortifacient on day 9 when given every 8 hours i.v., but not p.o., as evidenced by the following table:

| Treatment mg/kg × 3 on Day 9 | Route | No. Rats | Fetuses | Resorptions | Total Implants |
|---|---|---|---|---|---|
| Control | — | 8 | 12.0 ± 1.3 | 0 | 12.0 ± 1.3 |
| AGP 100 | i.p. | 10 | 4.4 ± 2.2 | 8.9 ± 2.0 | 13.3 ± 0.6 |
| AGP 100 | p.o. | 5 | 13.8 ± 0.9 | 0.4 ± 0.4 | 14.2 ± 0.7 |
| AGP 100 | i.v. | 3 | 4.3 ± 4.3 | 10.3 ± 4.7 | 14.7 ± 0.7 |

In preliminary experiments using single s.c. doses of PGs on day 5 of pregnancy failed to induce abortion. However, when the compounds were injected twice daily (9 a.m. and 3 p.m.) in adequate doses on days 4–7 of gestation, implantation occured at the normal time but this was then followed by resorption of the embryos. $PGF_{2\alpha}$ appeared to be about twice as active as $PGE_1$ and $PGE_2$. Said results are evidenced by the following table:

| Treatment µg/rat s.c. × 2 daily days 4–7 | No. Rats | Fetuses | Resorptions | Total Implants |
|---|---|---|---|---|
| Control | 7 | 14.3 ± 0.6 | 0.1 ± 0.1 | 14.4 ± 0.5 |
| $PGF_{2\alpha}$ 100 | 5 | 14.2 ± 0.7 | 0 | 14.2 ± 0.7 |
| 200 | 5 | 14.4 ± 0.2 | 0.2 ± 0.2 | 14.6 ± 0.2 |
| 400 | 5 | 0 | 9.6 ± 2.6 | 9.6 ± 2.6 |
| $PGE_1$ 200 | 5 | 10.8 ± 2.7 | 0 | 10.8 ± 2.7 |
| 400 | 5 | 10.6 ± 2.7 | 0 | 10.6 ± 2.7 |
| 800 | 5 | 0 | 7.0 ± 1.9 | 7.0 ± 1.9 |
| $PGE_2$ 200 | 5 | 10.6 ± 2.8 | 0 | 10.6 ± 2.8 |
| 400 | 5 | 6.6 ± 2.8 | 0 | 6.6 ± 2.8 |
| 800 | 5 | 0 | 5.6 ± 2.6 | 5.6 ± 2.6 |

Administration of either AGP (30 mg/kg s.c. days 3–5 of pregnancy) or $PGF_{2\alpha}$ (1 mg/kg s.c. on day 5 of pregnancy) did not induce resorption of fetuses in rats. However, combined treatment with the two agents led to resorption of a preponderance of the fetuses as evidenced by the following table:

| Treatment mg/kg s.c. | Days | Rats | Fetuses | Resorptions | Total Implants |
|---|---|---|---|---|---|
| Control | — | 5 | 13.4 ± 0.9 | 0 | 13.4 ± 0.9 |
| AGP 30 | 3–5 | 5 | 12.2 ± 1.8 | 1.6 ± 1.1 | 13.8 ± 1.0 |
| $PGF_{2\alpha}$ 1 | 5 | 5 | 15.4 ± 0.6 | 0 | 15.4 ± 0.6 |
| AGP 30 + $PGF_{2\alpha}$ 1 | 3–5 5 | 5 | 3.2 ± 3.2 | 7.6 ± 2.0 | 10.8 ± 1.5 |

EXAMPLE 2

Preliminary experiments using oral doses of d-aminoglutethimide d-tartrate hemihydrate≡AGT (U.S. Pat. No. 3,944,671 Example 1) alone, and in combination with subcutaneous doses of 7-[3α-(3β-hydroxy-1-trans-4-m-trifluorophenoxy-butenyl)-4β-hydroxy-tetrahydro-2β-furyl]-heptanoic acid≡TPF revealed that AGT is 100% effective as antifertility agent at 500 mg/kg/p.o., and TPF 64% effective at 25 µg/animal/s.c. The combination of 100 mg/kg/p.o. of AGT and 10 µg/animal/s.c. of TPF is more effective than either agent alone at these doses as evidenced by the following table:

| PERCENT OF LITTER LIVING | | | | |
|---|---|---|---|---|
| AGT mg/kg/p.o. day 3–5 | TPF µg s.c. day 5 of pregnancy | | | |
| | 0 | 5 | 10 | 25 |
| 0 mg | 100% | 98% | 70% | 36% |
| 100 | 90 | 92 | 33 | — |
| 250 | 68 | 65 | 0 | — |
| 500 | 0 | 37 | 0 | — |

Said active ingredients are administered in admixture with the following excipients:

AGT + 3% corn starch + 5% polyethylene glycol 400 + 1 drop of polysorbate 80 per 10 ml of distilled water.

TPF 10 mg per 0.1 ml of ethanol, which solution is diluted with the buffer prepared from 19 ml of 0.2M aqueous monosodium phosphate and 81 ml of 0.2M aqueous disodium phosphate, corrected with the latter to the pH = 7.4.

Said compositions are administered to pregnant Lakeview hamsters arriving at day 1 postcoitus, which are maintained in a day-night reversed room (11 A.M. to 11 P.M.). Food and water is given ad libitum. Six hamsters per group are used (3 per cage) and each test is carried out with a control group receiving said excipients only. The orally administered AGT is given for 3 consecutive days starting on day 3 postcoitus, at a rate of 5 ml/kg body weight, and these animals are sacrificed on day 10 to 12 postcoitus. The subcutaneously administered TPF is given once on day 5 postcoitus only, at a volume of 0.2 ml per animal, and these animals are sacrificed on day 8 postcoitus. The uterus of each animal is inspected and implantation sites are counted and recorded according to viable or resorbed fetuses. Percent inhibition is determined by comparison of treated groups over the control group.

Said TPF is also orally effective and the approximative 50% effective doses ($ED_{50}$) for antifertility effects in pregnant hamsters are these:

| Agent | $ED_{50}$ s.c. | $ED_{50}$ oral |
|---|---|---|
| $PGF_{2\alpha}$ | 0.1 mg/kg | 7.5 mg/kg |
| $PGE_2$ | 2.0 mg/kg | — |
| TPF | 0.1 mg/kg | 0.31 mg/kg |

Accordingly, TPF is about 10–20 times more potent orally than $PGF_{2\alpha}$. It is also active in rats and rabbits.

Said TPF can be prepared as follows: The mixture of 56 g of 7-[3-hydroxymethyl-4-(2-tetrahydropyranyloxy)-tetrahydro-2-furyl]-heptanoic acid nitrile (U.S. Pat. No. 3,883,659, Column 13), 150 ml of methanol, 75 ml of water and 75.5 ml of 20% aqueous potassium hydroxide is heated in a sealed tube to 115°–120° for 48 hours and evaporated. The residue is taken up in 100 ml of water and 100 ml of saturated aqueous sodium chloride, the mixture neutralized with dry ice and extracted 6 times with diethyl ether. The extract is dried, evaporated, the residue dissolved in diethyl ether and heated with ethereal diazomethane until the discoloration ceases. The mixture is evaporated, to give the 7-[3-hydroxymethyl-4-(2-tetrahydropyranyloxy)-tetrahydro-2-furyl]-heptanoic acid methyl ester.

To the solution of 13 g thereof in 2 lt. of methylene chloride, 61 g of pyridine chromium trioxide complex are added at once and the mixture is stirred at room temperature for 15 minutes. It is washed with water, dried, treated with charcoal, filtered and evaporated, to yield the 2-(6-carbomethoxyhexyl)-4-(2-tetrahydropyranyloxy)-tetrahydrofurane-3-carboxaldehyde.

The solution of 12.07 g thereof in 25 ml of dimethoxyethane is added at once to the solution made by adding 13.7 g of dimethoxy-[3-(m-trifluoromethylphenoxy)-2-oxo-propyl]-phosphonate to the suspension of 1.68 g of sodium hydride in 280 ml of dimethoxyethane, and stirring the mixture for two hours. The whole mixture is stirred at room temperature overnight and evaporated. The residue is taken up in diethyl ether and the solution washed with water. The organic layer is dried, evaporated and the residue subjected to preparative thin layer chromatography on silica gel plates (1 mm thick), which are eluted with ethyl acetate-methylene chloride (1:4), to yield the 7-[3α-(3-oxo-4-(m-trifluoromethylphenoxy)-1-trans-butenyl)-4β-(2-tetrahydropyranyloxy)-tetrahydro-2β-furyl]-heptanoic acid methyl ester, having Rf = 0.5. (The corresponding 4α-tetrahydropyranyloxy epimer has Rf = 0.43).

To the solution of 4.74 g thereof in 100 ml of ethanol, 1.02 g of sodium borohydride are added while stirring at 0°. After ½ hour, the mixture is poured into ice-water, extracted with diethyl ether, the extract washed with water and saturated aqueous sodium chloride, dried and evaporated to yield the 7-[3α-(3-hydroxy-4-(m-trifluoromethylphenoxy)-1-trans-butenyl)-4β-(2-tetrahydropyranyloxy)-tetrahydro-2β-furyl]-heptanoic acid methyl ester.

To the solution of 4.54 g thereof in 50 ml of methanol, 50 mg of p-toluenesulfonic acid are added and the mixture allowed to stand at room temperature overnight. It is evaporated, the residue taken up in water, the mixture extracted with diethyl ether, the extract washed with water and saturated aqueous sodium chloride, dried and evaporated. The residue is chromotographed on 200 g of silica gel and eluted with ethyl acetate-methylene chloride (1:1). Of the two main fractions the slower moving isomer is the 7-[3α(3β-hydroxy-4-(m-trifluoromethylphenoxy)-1-trans-butenyl)-4β-hydroxy-tetrahydro-2β-furyl]-heptanoic acid methyl ester.

The mixture of 1.75 g thereof, 18 ml of methanol and 6 ml of N aqueous, sodium hydroxide is stirred at room temperature overnight, and evaporated. The residue is taken up in 20 ml of water and 20 ml of saturated aqueous sodium chloride, neutralized with N hydrochloric acid and extracted 5 times with diethyl ether. The extract is dried and evaporated, to yield the 7-[3α-(3β-hydroxy-4-(m-trifluoromethylphenoxy)-1-trans-butenyl)-4β-hydroxy-tetrahydro-2β-furyl]-heptanoic acid of the formula

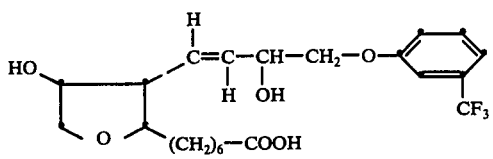

having Rf = 0.439 on silica gel eluted with benzene-dioxane-acetic acid (10:10:0.5).

The corresponding 3α-hydroxy-epimer is analogously synthesized from the corresponding ester and has Rf = 0.461.

The corresponding 4α,3α- and 4α,3β-dihydroxy-analogs have Rf = 0.463 and 0.425 respectively.

EXAMPLE 3

Preparation of injection ampuls each containing 10 and 300 mg of the active ingredients:

| Formula: | |
|---|---|
| Aminoglutethimide phosphate | 1,020 g |
| Prostaglandin F$_{2\alpha}$ | 34 g |
| 1,1,1-Trichloro-2-methyl-2-propanol | 85 g |
| Polysorbate 80 | 85 g |
| Methylcellulose 100 cps | 1,785 g |
| Sodium carboxymethylcellulose 70 MV | 51 g |
| Sodium chloride | 136 g |
| Water for injection | 17 lt. |

PROCEDURE

The chloropropanol is first dissolved in 13 lt of water at 90°, then the sodium carboxymethylcellulose is added while stirring, followed by the methylcellulose and stirring is continued for 15 minutes. The mixture is allowed to stand at 10° for 12 hours, combined with the polysorbate, AGP and the solution of the sodium chloride and PGF$_{2\alpha}$ in 250 ml of water each. The resulting solution is made up to 17 lt with water, adjusted with sodium hydroxide to pH = 7.4, filtered through a sintered glass funnel, the filtrate placed into 2 lt sterilized bottles, steam-sterilized at 100° for 3.25 hours and filled into 5 ml ampuls with standard equipment.

In the analogous manner solutions of the other active ingredients, mentioned in the outset, are prepared from equivalent amounts thereof.

EXAMPLE 4

Preparation of 1,000 capsules each containing 20 and 200 mg of the active ingredients:

| Formula: | |
|---|---|
| 7-[3α-(3β-hydroxy-1-trans-4-m-trifluorophenoxy-butenyl)-4β-hydroxy-tetrahydro-2β-furyl]-heptanoic acid | 20.00 g |
| d-aminoglutethimide d-tartrate hemihydrate | 200.00 g |
| Lactose | 150.00 g |
| Talcum powder | 30.00 g |

PROCEDURE

All the powders are passed through a screen with openings of 0.6 mm. Then the drug substances are placed in a suitable mixer and mixed first with the talcum, then with the lactose until homogeneous. No. 1 hard gelatin capsules are filled with 400 mg each, using a capsule filling machine.

Analogously capsules are prepared from the other compounds illustrated herein.

I claim:

1. A pharmaceutical antifertility composition comprising: (a) a pharmacological amount of an α-(4-aminophenyl)-α-lower alkylglutarimide, or its lower alkanoyl derivative corresponding to Formula I

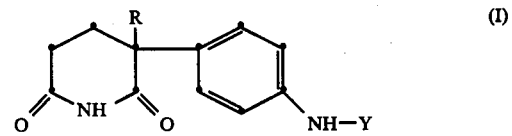

wherein R is lower alkyl and Y is hydrogen or lower alkanoyl, or a therapeutically acceptable acid addition salt thereof; (b) a pharmacological amount of a natural prostaglandin, or analogs thereof corresponding to Formula II

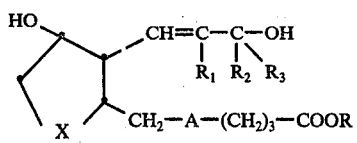

wherein A is methylene, ethylene or ethenylene, X is carbonyl, hydroxymethylene, oxa, thia, sulfinyl or sulfonyl, each of $R_1$ and $R_2$ is hydrogen or lower alkyl, each of R and $R_3$ are an aliphatic, cycloaliphatic, cycloaliphatic-aliphatic or araliphatic radical or R is hydrogen or one base-equivalent, whereby both of said amounts together are so selected to cause interception in mammals and (c) a pharmaceutical excipient for oral or parenteral administration.

2. A composition as claimed in claim 1, wherein such compounds of Formula I, or their therapeutically acceptable acid addition salts are used, in which R is alkyl with up to 4 carbon atoms and Y is hydrogen, and such compounds of Formula II are used, in which each of R and $R_3$ is lower alkyl, lower alkenyl, lower alkynyl, (3 to 7 ring-membered cycloalkyl or cycloalkenyl)-$C_mH_{2m}$ wherein $m$ is an integer from 0 to 4, (Ph, PhO or Hc)-$C_nH_{2n}$, wherein Ph is phenyl, (lower alkyl)-phenyl, (lower alkoxy)-phenyl, (lower alkylenedioxy)-phenyl, (halogeno)-phenyl, (trifluoromethyl)-phenyl, (nitro)-phenyl or (di-lower alkylamino)-phenyl, Hc is furyl or thienyl and $n$ is an integer from 1 to 4, R is also hydrogen, an alkali metal or one equivalent of an alkaline earth metal and $R_3$ is also (lower alkoxy or halo)-lower alkyl, A is ethylene or ethenylene, $R_1$ and $R_2$ are hydrogen or lower alkyl, and X is carbonyl, hydroxymethylene, oxa, thia, sulfinyl or sulfonyl.

3. A composition as claimed in claim 1, wherein such compounds of Formula I, or their therapeutically acceptable acid addition salts, or the dextrorotatory antipodes thereof are used, in which R is ethyl and Y is hydrogen, and such compounds of Formula II are used, in which R is hydrogen, sodium, potassium or alkyl with up to 4 carbon atomes, each of $R_1$ and $R_2$ is hydrogen, A is ehtylene or cis-ethenylene, X is carbonyl, $\beta$-hydroxymethylene, oxa, thia, sulfinyl or sulfonyl, and $R_3$ is n-(pentyl), pent-2-enyl, hexyl or heptyl), (cyclopropyl, cyclopentyl, cyclohexyl, Ph', Ph'O, or 2-furyl)-methyl or -ethyl, wherein Ph' is phenyl, tolyl, anisyl, fluorophenyl, chlorophenyl or trifluoromethylphenyl.

4. A composition as claimed in claim 1, wherein aminoglutethimide, its dextrorotatory antipode or a therapeutically acceptable acid addition salt is used as compound I, and prostaglandin $F_{2\alpha}$ or 7-[3$\beta$-hydroxy-4-m-trifluoromethylphenoxy-1-trans-butenyl)-4$\beta$-hydroxy-tetrahydro-2$\beta$-furyl]-heptanoic acid or an alkali metal salt thereof is used as compound II.

5. A composition as claimed in claim 1, wherein about 2 to 50% of compounds I and II are admixed to an orally or parenterally useful excipient.

6. A method of terminating pregnancy in mammals, which comprises administering to a mated or impregnated female mammal orally or parenterally a single or multiple dose of said composition claimed in claim 1.

7. A method as claimed in claim 6, wherein about 0.1 to 50 mg/kg/day of compounds I and about 0.001 to 1 mg/kg/day of compounds II are administered.

8. A method as claimed in claim 6, wherein about 0.1 to 10 mg/kg/day of compounds I and about 0.001 to 0.1 mg/kg/day of compounds II are administered.

9. A method as claimed in claim 6, wherein said compositions are administered at most for 3 consecutive days during days 1 to 30 after mating and/or after a missed menses.

* * * * *